United States Patent
Kato (10) Patent No.: US 10,245,060 B2
(45) Date of Patent: Apr. 2, 2019

(54) EDGED MEDICAL CUTTING TOOL (71) Applicant: MANI, INC., Utsunomiya-shi, Tochigi (JP)

(72) Inventor: Kazuaki Kato, Utsunomiya (JP)

(73) Assignee: MANI, INC., Utsunomiya-Shi, Tochigi (JP)

( * ) Notice: Subject to any disclaimer, the term of this patent is extended or adjusted under 35 U.S.C. 154(b) by 586 days.

(21) Appl. No.: 14/940,318

(22) Filed: Nov. 13, 2015

(65) Prior Publication Data
US 2016/0066941 A1   Mar. 10, 2016

Related U.S. Application Data

(63) Continuation of application No. 13/876,739, filed as application No. PCT/JP2011/071832 on Sep. 26, 2011.

(30) Foreign Application Priority Data

Sep. 28, 2010   (JP) .................................. 2010-217040

(51) Int. Cl.
   *C25F 3/24*       (2006.01)
   *A61B 17/00*      (2006.01)
   (Continued)

(52) U.S. Cl.
   CPC ........ *A61B 17/32* (2013.01); *A61B 17/06066* (2013.01); *A61B 17/3211* (2013.01);
   (Continued)

(58) Field of Classification Search
   None
   See application file for complete search history.

(56) References Cited

U.S. PATENT DOCUMENTS 4,026,737 A * 5/1977 Takahari ................. C23C 22/77
                                                           148/241
5,202,013 A    4/1993 Chamberlain et al.
   (Continued)

FOREIGN PATENT DOCUMENTS

| JP | 06-49216     | 6/1994  |
| JP | 2002-345834  | 12/2002 |
| JP | 2006-51147   | 2/2006  |

OTHER PUBLICATIONS

International Search Report directed to International Patent Application No. PCT/JP2011/071832, 2 pages including English translation dated Oct. 18, 2011.

*Primary Examiner* — Nicholas A Smith
(74) *Attorney, Agent, or Firm* — Shlesinger, Arkwright & Garvey LLP (57) ABSTRACT

[Problem] To provide a medical cutting tool with low impalement resistance. [Solution] The edged medical cutting tool comprising a knife, trocar or cutting suture needle has a sharp edge (1) for incising living tissue and a flat part (2) that configures the edge, and the color of the portion of the flat part (2a) along the edge (1) differs from the color of the rest of the flat part (2b). The difference in color results from a difference in the thickness of an oxide film. Another edged medical cutting tool is configured of austenite stainless steel and has a sharp edge (1) for incising living tissue and a flat part (2) that configures the edge. The chrome content of the portion of the flat part (2a) along the edge is higher than the chrome content of the rest of the flat part (2b).

1 Claim, 4 Drawing Sheets (51) Int. Cl.
  *A61B 17/06* (2006.01)
  *A61B 17/32* (2006.01)
  *A61F 9/013* (2006.01)
  *A61B 17/3211* (2006.01)

(52) U.S. Cl.
  CPC ...... *C25F 3/24* (2013.01); *A61B 2017/00526* (2013.01); *A61F 9/0133* (2013.01); *A61F 2250/005* (2013.01)

(56) References Cited

U.S. PATENT DOCUMENTS

| | | | |
|---|---|---|---|
| 5,224,950 A | | 7/1993 | Prywes |
| 5,263,974 A | * | 11/1993 | Matsutani .............. A61B 17/00 606/222 |
| 5,958,519 A | | 9/1999 | Wang et al. |
| 6,330,750 B1 | | 12/2001 | Meckel |
| 2003/0004527 A1 | | 1/2003 | Matsutani et al. |
| 2007/0179515 A1 | | 8/2007 | Matsutani et al. |
| 2009/0048537 A1 | | 2/2009 | Lydon et al. |

\* cited by examiner

EDGED MEDICAL CUTTING TOOL

TECHNICAL FIELD

The present invention relates to a sharply-edged medical cutting tool for incising a biological tissue with an improved piercing property.

BACKGROUND

At the time of an ophthalmic surgical operation, a knife or trocar is employed to pierce an eyeball or incise a cornea or sclera, and a suture needle for piercing or incising a muscle or a skin is employed to suture an affected area. A medical cutting tool such a knife, a trocar, or a suture needle includes a sharp tip, a sharp edge elongated from the sharp tip, a plane portion that forms the edge, and a body portion continuously elongated from the plane portion.

The edge and the plane portion have cross sections having a polygonal shape such as a triangle, a rectangle, or a pentagon. The shape of the cross section is set according to a type of a desired medical cutting tool, that is, according to whether the medical cutting tool is a knife, a trocar, or a suture needle. In addition, regardless of the cross-sectional shape of the medical cutting tool, two edges are formed by using the sharp tip as a starting point (for example, see Patent Literature 1).

CITATION LIST

Patent Literature

Patent Literature 1: Japanese Patent Publication No. 06-49216 B2.

SUMMARY OF INVENTION

Technical Problem

In the medical cutting tool having the aforementioned configuration, it is necessary to reduce impalement resistance generated during the incision of the affected area. For example, if the impalement resistance is large, a doctor may feel fatigued, and may not accurately perform a surgical operation. For this reason, a manufacturer of a medical cutting tool has an important issue to improve a medical cutting tool including a knife, a trocar, and a suture needle having reduced impalement resistance.

The present invention provides an edged medical cutting tool having reduced impalement resistance.

Solution to Problem

In order to address the aforementioned problem, the inventors have made many development experiments. As a result, the inventors have found a fact that the impalement resistance is reduced by providing a sharp edge. In addition, the inventors have recognized that the sharp edge can be implemented by performing an electrolytic polishing process or a chemical polishing process within a short time after a polishing process.

The inventors have also recognized that a color of one plane portion along the edge is different from that of the other plane portion when the sharp edge is configured by performing an electrolytic polishing process or a chemical polishing process and the polishing process is performed within a short time. Furthermore, the inventors have also recognized that the chromium content of one plane portion along the edge is different from that of the other plane portion when a stainless steel is employed as a material.

According to an aspect of the present invention, there is provided a medical cutting tool including: a sharp edge for incising a biological tissue; and plane portions that form the edge, wherein a color of one plane portion along the edge is different from that of the other plane portion.

In the edged medical cutting tool described above, a color difference between one plane portion along the edge and the other plane portion is based on a thickness difference of an oxide film.

According to another aspect of the present invention, there is provided an edged medical cutting tool made of an austenitic stainless steel, including: a sharp edge for incising a biological tissue; and plane portions that form the edge, wherein a chromium content of one plane portion along the edge is larger than a chromium content of the other plane portion.

Advantageous Effects of Invention

In the edged medical cutting tool (hereinafter, simply referred to as a cutting tool) according to the present invention, it is possible to reduce impalement resistance by forming a sharp edge. Therefore, during an ophthalmic surgical operation or a general surgical operation, it is possible to alleviate fatigue of a doctor and accurately perform the incision.

Particularly, since the formation of the sharp edge can be recognized by checking a color difference between one plane portion along the edge and the other plane portion out of the flat portions that form the edge of the cutting tool, it is possible to perform accurate inspection at least when the cutting tool is manufactured.

In addition, in another cutting tool according to the present invention, by comparing the chromium content of one plane portion along the edge with the chromium content of the other plane portion, it is possible to check whether or not the sharp edge is formed.

REFERENCE SIGNS LIST

A: TROCAR
1: EDGE
2, 2a, 2b: PLANE PORTION
3: RIDGE
4: SHARP TIP
5: BODY PORTION
6: BOUNDARY
7: SMALL PLANE PORTION
10: DASHED-DOTTED LINE (boundary between the plane portion 2a and the other plane portion 2b)

DESCRIPTION OF EMBODIMENTS

Hereinafter, a cutting tool according to the present invention will be described. According to the present invention, when a biological tissue is pierced and incised during a surgical operation using a knife, a trocar, an edged suture needle, and the like, impalement resistance is reduced, so that it is possible to alleviate fatigue of a doctor and accurately perform the surgical operation.

According to the present invention, a sharp edge for incising a biological tissue is configured by causing two planes to intersect each other. In addition, a color of one plane portion along the edge is different from that of the other plane portion. This color difference corresponds to a thickness difference of an oxide film, which is caused by reducing a processing time in an electrolytic polishing process or a chemical polishing process (electrolytic polishing or the like) performed during a cutting tool manufacturing procedure.

In other words, since burrs attached to the edge are large in the case of a medical cutting tool manufactured in the related art, it is necessary to perform an electrolytic polishing or the like for a long time in order to remove the burrs from the edge. In addition, due to the long-time electrolytic polishing or the like, elution also occurs in a portion along the edge when the burrs attached to the edge are removed. As a result, fine roundness is generated at a pointed end of the edge, so that sharpness of the edge disappears.

On the contrary, in a procedure of manufacturing a cutting tool according to the present invention, the burrs attached to the edge are removed by using short-time electrolytic polishing or the like, so that a sharp edge can be implemented. In addition, as a result of the short-time electrolytic polishing or the like, a thickness difference of an oxide film occurs between one plane portion along the edge and the other plane portion, and a color difference occurs due to the thickness difference of the oxide film.

In the cutting tool where a color difference occurs between one plane portion along the edge and the other plane portion as described above, a change in material component also occurs in addition to the color difference.

Therefore, the cutting tool according to the present invention can be recognized by the color difference between one plane portion along the edge and the other plane portion or by quantitatively analyzing the material components.

Furthermore, in the cutting tool according to the present invention, it is possible to sufficiently reduce the impalement resistance in comparison with that of the cutting tool typically used in the related art.

As a material for the cutting tool according to the present invention, a metal represented by a carbon steel or a martensitic stainless steel which can be expected to be hardened through thermal treatment or an austenitic stainless steel which cannot be expected to be hardened through thermal treatment can be selectively used. In addition, it is preferable that the cutting tool according to the present invention be configured by performing a shaping process and a hardening process for a desired cutting tool through processes optimized to the selected material.

Figure 1:
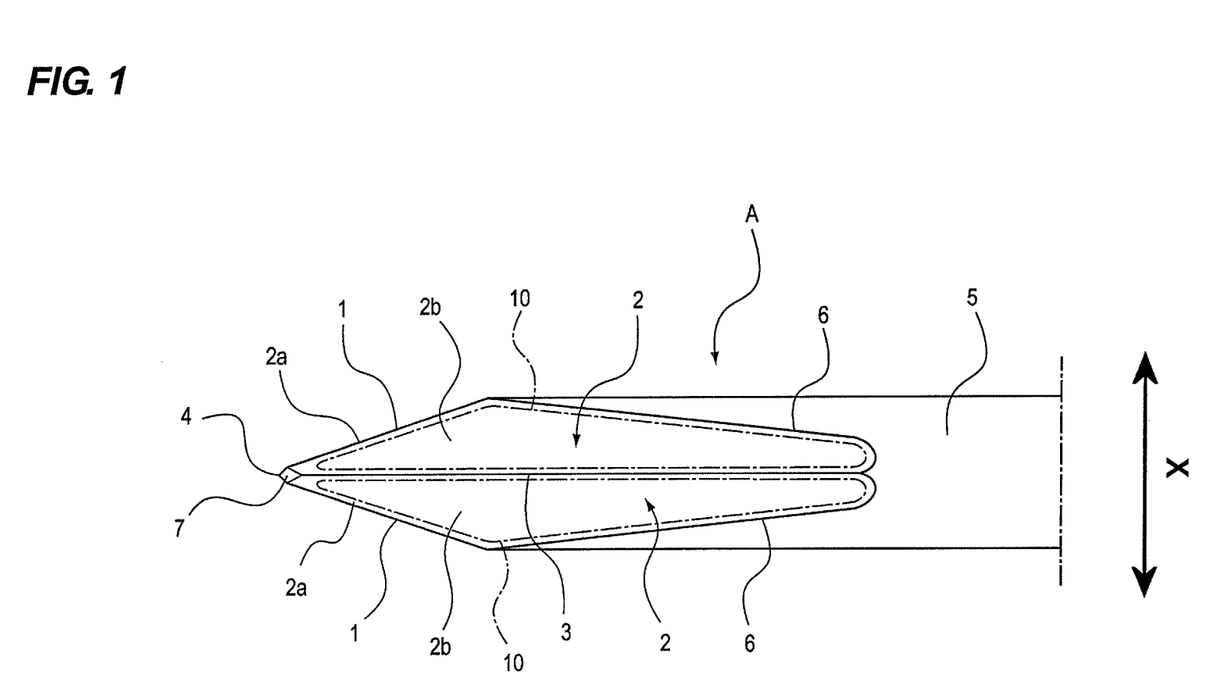
FIG. 1 is a diagram illustrating a trocar as a cutting tool according to an embodiment.
Figure 2:
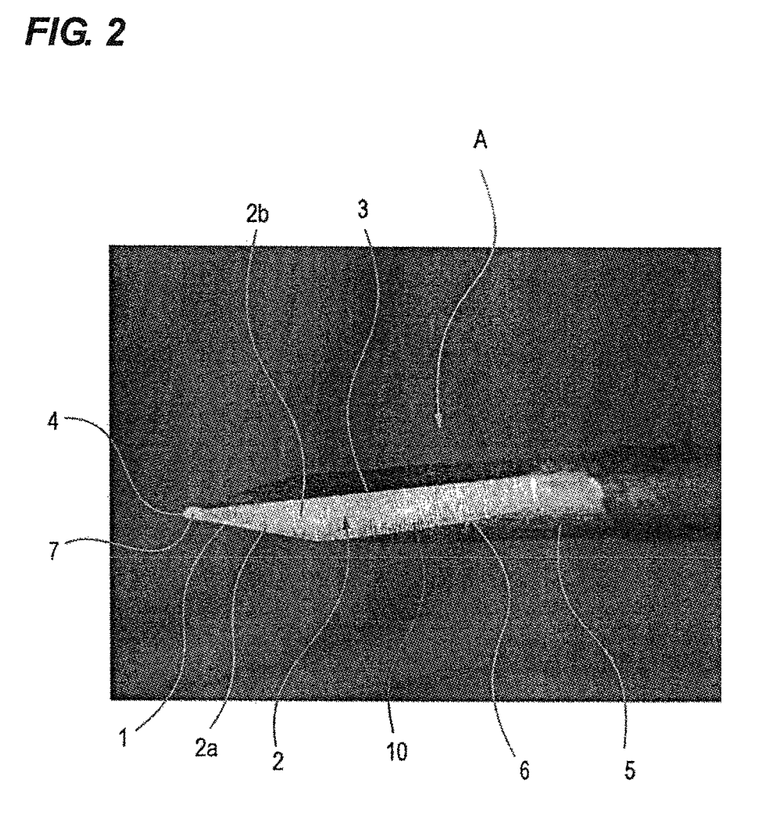
FIG. 2 is a photographic image of the trocar illustrated in FIG. 1.

Next, a trocar A according to the present embodiment will be described with reference to FIGS. 1 and 2. The trocar A illustrated in FIGS. 1 and 2 is a cutting tool for piercing an eyeball and cutting a cornea or sclera in an ophthalmic surgical operation. As a material of the trocar A, SUS302 that is an austenitic stainless steel is employed. The trocar A is formed in a round bar shape having a fiber-like extending structure by performing a cold drawing process on an element wire with a predetermined area reduction rate and having a high strength through a fabrication and hardening process.

In addition, the trocar A is configured in a straight needle shape by performing a press process and then performing a grinding process on an end portion of the round-bar-shaped material fabricated as described above or by directly performing the grinding process on the end portion. Incidentally, as the cutting tool according to the present invention, in addition to the trocar A according to the present embodiment, there are an edged suture needle, a knife, and the like having a cutting functionality and any of them may be formed in the configuration of the trocar A described below.

In FIGS. 1 and 2, the trocar A includes a pair of sharp edges 1 formed by causing two plane portions 2 including a plane portion 2 illustrated in FIG. 1 and a plane portion (not illustrated) on the rear side of the paper of FIG. 1 to intersect each other. Particularly, in the trocar A according to the embodiment, a cross section (a transverse cross section of a portion where the edge 1 of the trocar A exists) of a portion corresponding to the edge 1 is formed in a rhombus shape. The pair of edges 1 are formed on the two sides in the width direction (in the arrow direction X in FIG. 1), and the pair of ridges 3 having no incising function are formed on the two sides in the thickness direction (direction perpendicular to the paper plane of FIG. 1) perpendicular to the width direction. In addition, the rear surface side of the trocar A illustrated in FIG. 1 has the same shape as that illustrated in FIG. 1.

The edge 1 and the plane portion 2 are formed to converge toward a sharp tip 4. In other words, the edge 1 and the plane portion 2 are inclined by using the sharp tip 4 as a starting point. Therefore, the pair of edges 1, the pair of ridges 3, and the plane portions 2 that forms the edges 1 and the ridges 3 are separated from each other according to the respective inclination and are connected to the body portion 5. The body portion 5 is formed in a round bar shape having a predetermined diameter, so that the trocar A is formed in a straight needle shape.

In the trocar A having the aforementioned configuration, as the plane portion 2 that forms the edge 1 is separated from the edge 1 and is connected to the body portion 5, a boundary 6 is formed between the plane portion 2 and the body portion 5. The boundary 6 forms an edge having an obtuse angle by causing the plane portion 2 and the outer circumferential surface of the body portion 5 to intersect each other.

In addition, in the trocar A according to the present embodiment, a small plane portion 7 is formed on the sharp tip 4 sides of the two plane portions 2 formed on one side in the thickness direction. By forming the small plane portion 7, the sharp tip 4 is configured from three planes including the two plane portions 2 and the small plane portion 7. Therefore, the sharp tip 4 is formed necessarily as one point, so that it is possible to improve positioning accuracy at the first time of impalement of a tissue and reduce the impalement resistance.

As illustrated in FIG. 2, a part of the plane portions 2 along the edge 1, that is, a plane portion 2a (one plane portion 2a) formed between the dashed-dotted line 10 and the edge 1 illustrated in FIGS. 1 and 2 has a color different from that of the other plane portion 2b. However, since it is difficult to clearly represent the color difference between the plane portions 2a and 2b by using a certain line as a boundary, the dashed-dotted line 10 indicates the boundary between the plane portion 2a and the other plane portion 2b for convenience purposes.

The inventors of the present invention have examined the cause of the color difference, and it have been determined that the color difference is generated due to a thickness difference of an oxide film between the plane portions 2a and 2b. In other words, since the oxide film in the plane portion 2a is thin, the color is relatively close to a color of a metal material. Since the oxide film in the plane portion 2b is thick, the color is close to gold. Incidentally, in the photographic image of FIG. 2, the plane portion 2a has a dark color, and the plane portion 2b has a white color. However, these color components are caused from illumination during the photographing.

As illustrated in FIG. 2, the plane portion 2a having a different color is formed in a part of the plane portion 2 along the edge 1, a portion along the boundary 6, and a portion along the ridge 3. In other words, the plane portion 2a is formed over the substantially entire area in the vicinity of the plane 2. However, in the case of the cutting tool, if the plane portion 2a having a color different from that of the other plane portion 2b is formed in a part of the plane portions 2 along the edge 1, it is possible to sufficiently reduce the impalement resistance.

Next, a procedure of manufacturing a trocar A capable of removing burrs attached to the edge 1 by using a short-time electrolytic polishing or the like will be described in brief.

As described above, the trocar A is formed as a rod-like material by cutting a round bar material, which is made of an austenitic stainless steel having a predetermined strength through a cold drawing process, by a desired length. Then, by performing a press process on the end portion on the one side of the material, the cross section is formed in a rhombus shape. The formed portion is ground to form a plane portion 2, so that an edge 1 is formed in an intersection between the two plane portions 2. Furthermore, a ridge 3 is formed by an intersection portion between the two plane portions 2 or by a press-processed surface, and a boundary 6 is formed in an intersection between one plane portion 2 and the outer circumferential surface of the body portion 5.

Similarly to the aforementioned case, when the material is ground, burrs are inevitably attached to the edge 1, the ridge 3, and the boundary 6 between the plane portion 2 and the body portion 5. Therefore, by reducing at least the burrs attached to the edge 1, it is possible to remove the burrs through a short-time electrolytic polishing process or the like. In this manner, in order to reduce the attached burrs, a processing rate during the grinding process is reduced.

The reduction of the processing rate can be implemented by decreasing a load to the material during the grinding process. For example, if a processing rate at the time of grinding is set to about 1/10 of the processing rate at the time of grinding of the trocar in the related art, the burrs attached to the edge 1 can be sufficiently reduced. However, the processing rate is not limited to a specific value, but it may be appropriately set depending on a target cutting tool.

When the burrs attached to the edge 1 are reduced by reducing the processing rate at the time of grinding, the burrs can be removed within a short time by performing a polishing process such as an electrolytic polishing. As a result, it is possible to reduce a processing time of the electrolytic polishing or the like. As the processing time of the electrolytic polishing or the like is reduced, the polishing is not uniformly performed on the plane portion 2, but irregularity occurs in the polishing process. In other words, a difference is generated in a degree of polishing between the plane portion 2a along the edge 1 and the other plane portion 2b.

The partial difference in a degree of polishing in the plane portion 2 is caused from a thickness difference in an oxide film, a difference in a material component, and a difference in surface roughness. In other words, since the material is thin in the plane portion 2a along the edge 1, the electrolytic polishing or the like progresses at a high speed, so that the elution amount of iron increases and the chromium content increases. Therefore, the oxide film thereof becomes thin, and the surface roughness is reduced. On the contrary, in the other plane portion 2b, since the material is thick in comparison with the plane portion 2a, the electrolytic polishing or the like is performed at a low speed in comparison with the plane portion 2a, so that the elution amount of iron decreases and the chromium content decreases. Therefore, the oxide film thereof becomes thick, and the surface roughness increases.

In this manner, the color of plane portion 2a along the edge 1 is different from that of the other plane portion 2b due to a thickness difference of an oxide film, so that the chromium content of the plane portion 2a is larger than the chromium content of the plane portion 2b.

Figure 3:
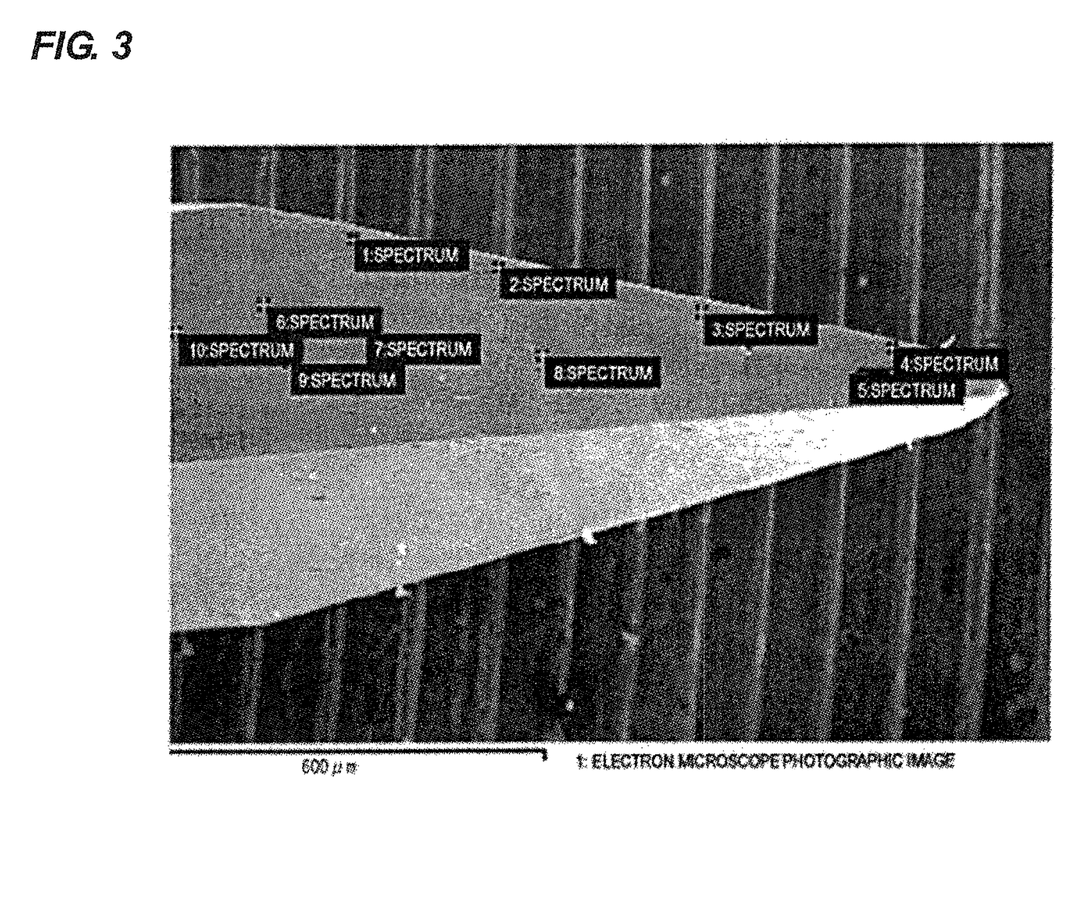
FIG. 3 is a photographic image illustrating sampling positions when material components of a trocar are quantitatively analyzed.
Figure 4:
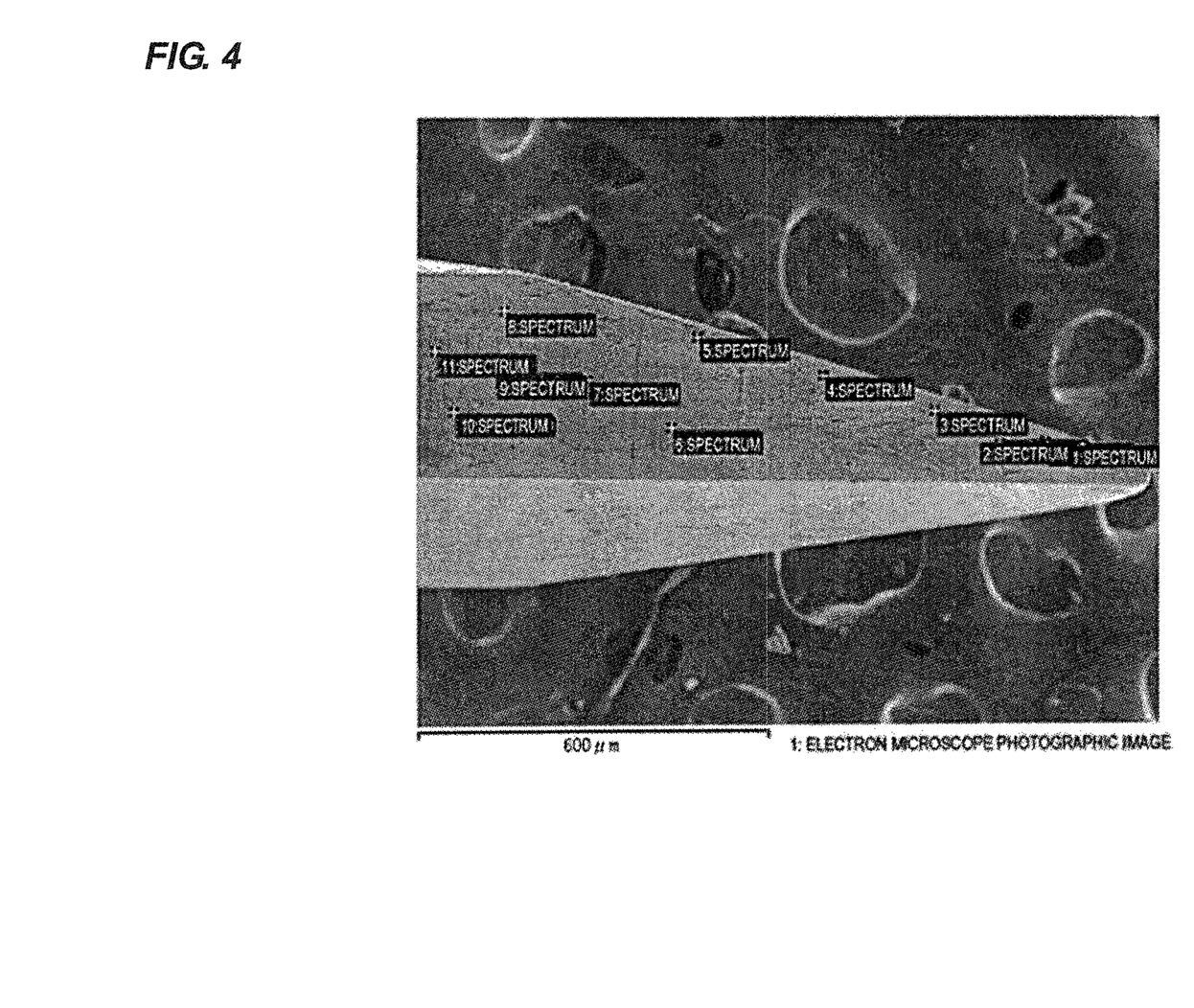
FIG. 4 is a photographic image illustrating sampling positions when material components of a trocar as a comparative example are quantitatively analyzed.

Next, the description will be made for a result of the comparison between the trocar A according to the present embodiment and the trocar in the related art (comparative example). FIG. 3 is a diagram illustrating the trocar A according to the present embodiment and sampling positions for quantitative analysis of metal components. FIG. 4 is a diagram illustrating the trocar according to the comparative example and sampling positions for quantitative analysis of metal components. Spectra 1 to 5 are arranged on the flat portion along the edge, and spectra 6 to 10 are arranged on the other plane portion.

According to the present embodiment, an electrolytic polishing process was performed for the material subjected to the planar grinding. The electrolytic polishing was performed such that the entire length of the plane portion 2 was immersed for about 35 seconds, and then, the length portion corresponding to the edge 1 was immersed for about 5 seconds. Through the electrolytic polishing process, all the burrs attached to the edge 1 were removed. After the electrolytic polishing was completed, the quantitative analysis using X-ray analysis was performed for the spectra 1 to 10.

As a result, in the spectrum 1, the chromium content was 31.38%; the iron content was 60.08%; and the nickel content was 8.64%. In addition, in the spectrum 2, the chromium content was 31.45%; the iron content was 59.36%; and the nickel content was 9.19%. In addition, in the spectrum 3, the chromium content was 31.75%; the iron content was 60.10%; and the nickel content was 8.15%. In addition, in the spectrum 4, the chromium content was 29.10%; the iron content was 61.33%; and the nickel content was 9.57%. In addition, in the spectrum 5, the chromium content was 28.035%; the iron content was 63.41%; and the nickel content was 8.56%.

In the spectrum 6, the chromium content was 26.55%; the iron content was 63.57%; and the nickel content was 9.88%. In addition, in the spectrum 7, the chromium content was 26.47%; the iron content was 63.17%; and the nickel content was 10.36%. In addition, in the spectrum 8, the chromium content was 28.49%; the iron content was 61.47%; and the nickel content was 10.04%. In addition, in the spectrum 9, the chromium content was 27.40%; the iron content was 62.32%; and the nickel content was 10.28%. In addition, in the spectrum 10, the chromium content was 25.07%; the iron content was 65.16%; and the nickel content was 9.77%.

From the result described above, it can be said that the chromium content of the plane portion 2a along the edge 1 is larger that that of the other plane portion 2b (the spectra 6 to 10). Particularly, it is conceived that, in the spectra 1 to 3, since the thin edge 1 is formed only by the two plane portions 2, the elution amount of iron increases, so that the chromium content increases (31.38%, 31.45%, and 31.75%). It is conceived that, in the spectra 4 and 5, since the four plane portions approach each other, the relatively thick edge 1 is formed, so that the elution amount of iron is reduced and the chromium content is reduced (29.10% and 28.035%).

Here, out of the plane portion 2a, the chromium content (31.38%) of the spectrum 1 as a portion where the thin edge 1 is formed only along the two plane portions 2 and the chromium content (26.55%, 26.47%, 28.49%, 27.40%, and 25.07%) of the spectra 6 to 10 were compared. As a result, there were differences of 4.83%, 4.91%, 2.89%, 3.98%, and 6.31%, respectively.

In summary, it can be concluded that the chromium content of the portion (positions of the spectra 1 to 3, particularly, the width range within 40 μm in the vertical direction of the edge 1) where the thin edge 1 is formed only along the two plane portions 2 out of the plane portion 2a is larger than the chromium content of the pointed end portion (positions of the spectra 4 and 5) where the four plane portions approach each other. In addition, it can be concluded that the chromium content of the portion (positions of the spectra 1 to 3) is obviously larger than the chromium content of plane portion 2b (particularly, the portion separated by 100 μm or longer in the vertical direction of the edge 1).

Next, in the comparative example, the electrolytic polishing process was performed by immersing the entire, length of the plane portion for about 50 seconds with an electric current density higher than that of the aforementioned embodiment. Through this electrolytic polishing process, overall burrs attached to the edge were removed. After the electrolytic polishing was completed, the quantitative analysis was performed as in the embodiment.

As a result, in the spectrum 1, the chromium content was 27.70%; the iron content was 62.28%; and the nickel content was 9.02%. In addition, in the spectrum 2, the chromium content was 27.55%; the iron content was 62.47%; and the nickel content was 8.98%. In addition, in the spectrum 3, the chromium content was 26.55%; the iron content was 63.13%; and the nickel content was 9.32%. In addition, in the spectrum 4, the chromium content was 25.86%; the iron content was 62.95%; and the nickel content was 10.19%. In addition, in the spectrum 5, the chromium content was 25.22%; the iron content was 65.32%; and the nickel content was 9.46%.

In addition, in the spectrum 6, the chromium content was 25.87%; the iron content was 64.42%; and the nickel content was 9.71%. In addition, in the spectrum 7, the chromium content was 25.12%; the iron content was 65.00%; and the nickel content was 9.88%. In addition, in the spectrum 8, the chromium content was 25.79%; the iron content was 64.53%; and the nickel content was 9.68%. In addition, in the spectrum 9, the chromium content was 24.99%; the iron content was 65.16%; and the nickel content was 9.85%. In addition, in the spectrum 10, the chromium content was 26.26%; the iron content was 63.89%; and the nickel content was 9.85%.

In the comparative example described above, the electrolytic treatment time was sufficiently long, and the electrolytic polishing was performed uniformly over the entire area of the plane portion. Therefore, the elution amount of iron was also substantially uniform, and the chromium content was also substantially uniform.

In addition, in the plane portion along the edge in the comparative example, the chromium content of the portions (positions of the spectra 4, 5 and the like in the comparative example) where a thin edge is formed only along the two plane portions and the chromium content of the pointed end portions (positions of the spectra 1, 2 and the like in the comparative example) where the four plane portions approach each other were compared. As a result, the former portions were 25.86% and 25.22%, and the latter portions were 27.70% and 27.55%. On the contrary to the present embodiment, the portions where a thin edge was formed only along the two plane portions tended to be slightly small.

In the trocar A according to the present embodiment, the surface roughness of the plane portion 2a along the edge 1 and the surface roughness of the other plane portion 2b were measured. As a result, the average surface roughness of the plane portion 2a was Ra 2.38, and the average surface roughness of the plane portion 2b was Ra 3.15. It can be said that this difference is a significant difference in a medial cutting tool.

Next, an experiment of comparing impalement resistance between the trocar A according to the embodiment and the trocar (FIG. 4) according to the comparative example was performed. In this experiment, similar to a typical impalement experiment for a knife, a trocar, or a suture needle, a force for piercing a Porvair having a thickness of 0.45 mm was measured. Five samples of the trocar A and five samples of the trocar according to the comparative example were prepared. For each sample, the Porvair was pierced three times, and the average piercing force was obtained. In addition, the average value of overall piercing forces (that is, piercing of 15 times) was obtained, and comparison thereof was performed.

As a result, for the trocar A according to the present embodiment, the average impalement resistance was 96.6 mili-newton (mN), the maximum value of impalement resistance was 107.0 mN, and the minimum value of impalement resistance was 78.0 mN. On the contrary, for the trocar according to the comparative example, the average value of impalement resistance was 139.4 mN, the maximum value of impalement resistance was 158.3 mN, and the minimum value of impalement resistance was 118.3 mN.

In this manner, it can be said that the impalement performance of the trocar A according to the present embodiment is sufficiently improved in comparison with the impalement performance of the trocar in the related art or the trocar according to the comparative example.

INDUSTRIAL APPLICABILITY

The present invention can be usefully applied to a thinned knife, a trocar, or an edged suture needle used in an ophthalmic surgical operation or a neurosurgical operation.

The invention claimed is:

1. A method of producing a medical cutting tool for incising a biological tissue, the medical cutting tool being made of austenitic stainless steel, the method comprising the steps of:
   forming a medical cutting tool having a cutting edge and plane portions that form the cutting edge press working;
   performing an electrolytic polishing to the medical cutting tool formed by press working;
   detecting by quantitative analysis using X-ray analysis, after the electrolytic polishing, a first chromium content per unit mass of an area of the plane portions which is adjacent to the edge and a second chromium content per unit mass of the other area on the plane portions which is not adjacent to the edge; and determining that the cutting edge has sufficient sharpness when the first chromium content per unit mass is larger than the second chromium content per unit mass.

* * * * *